United States Patent [19]

Harris

[11] 4,404,407
[45] Sep. 13, 1983

[54] PROCESS FOR ENHANCING THE FRAGRANCE QUALITIES OF ETHYLENE GLYCOL MONOARYL ETHERS

[75] Inventor: Eugene G. Harris, West Chester, Ohio

[73] Assignee: Emery Industries, Inc., Cincinnati, Ohio

[21] Appl. No.: 271,730

[22] Filed: Jun. 8, 1981

[51] Int. Cl.$^3$ ................... C07C 41/34; C07C 41/38
[52] U.S. Cl. .................................................. 568/648
[58] Field of Search ................ 568/810, 648, 651, 914

[56] References Cited

U.S. PATENT DOCUMENTS

| 1,944,958 | 1/1934 | Valik et al. | 568/810 |
|---|---|---|---|
| 2,944,087 | 7/1960 | Nommensen et al. | 568/914 |
| 3,646,227 | 2/1972 | Grinstein | 568/914 |
| 3,865,880 | 2/1975 | Quelly et al. | 568/914 X |
| 4,107,099 | 8/1978 | Hedge | 568/914 X |

FOREIGN PATENT DOCUMENTS

| 1133556 | 7/1962 | Fed. Rep. of Germany . | |
| 981965 | 2/1965 | United Kingdom | 568/914 |

OTHER PUBLICATIONS

Brochure published by Ventron Corporation Chemicals Division "Hydride Chemicals for Process Stream Purification" 10, 11.

Primary Examiner—Bernard Helfin
Attorney, Agent, or Firm—Kenneth D. Tremain; Gerald A. Baracka

[57] ABSTRACT

Ethylene glycol monoaryl ethers useful as fragrance chemicals and substantially free of undesirable metallic notes are obtained by treating the product with an alkali metal borohydride at a temperature from ambient up to about 100° C.

6 Claims, No Drawings

PROCESS FOR ENHANCING THE FRAGRANCE QUALITIES OF ETHYLENE GLYCOL MONOARYL ETHERS

BACKGROUND OF THE INVENTION

1. Field of the Invention

The present invention relates to a process for enhancing the fragrance qualities of ethylene glycol monoaryl ethers and, particularly, ethylene glycol monophenyl ether.

2. Description of the Prior Art

Ethylene glycol monophenyl ether, also commonly referred to as phenoxyethanol, phenoxetol, and phenyl cellosolve, is a well known commercial product obtained by the reaction of phenol and ethylene oxide in an alkaline medium. Typical processes for the monoethoxylation of phenol are described in U.S. Pat. Nos. 2,852,566, 3,354,227, 3,364,267, 3,525,773, 3,642,911 and 3,644,534.

In addition to being a highly useful antimicrobial agent (see U.S. Pat. No. 2,451,149), ethylene glycol monophenyl ether has a mild rose odor and use for food, cosmetic and pharmaceutical applications is disclosed in U.S. Pat. Nos. 1,881,200 and 2,451,149. Utilization as a fragrance chemical has, however, been limited due to the "metallic" odor generally associated with the product. The presence of the metallic note is objectionable to perfumers as it masks the pleasant rose odor and subtle fresh green nuances. The malodorous constituent(s), whose source and nature are unknown, are not removed by commercial distillation processes. Even when high purity ethylene glycol monophenyl ether which is water-white and essentially free of catalyst residue, unreacted phenol and higher ethylene oxide adducts is obtained utilizing sophisticated laboratory distillation procedures, the undesirable metallic note may still be evident.

Treatment of various industrial aliphatic alcohols with alkali metal borohydrides is known. U.S. Pat. No. 2,867,651 discloses the treatment of alcohols obtained via the Oxo process with alkali metal borohydride to destroy undesirable color producing impurities and thus make it possible to obtain water-white esters suitable as resin plasticizers. The process of U.S. Pat. No. 2,957,023 describes a similar treatment of oxo alcohols with metallic borohydrides to obtain plasticizer esters having improved color, however, the alcohol containing the alkali metal borohydride is aged for at least one day prior to esterification. ALFOL alcohols are contacted with an alkaline borohydride at a temperature in the range 500° F. in accordance with the process of U.S. Pat. No. 3,860,520 to remove diols present as impurities and thus reduce the subsequent odor obtained when the alcohol is sulfated. There is no mention or suggestion in the above-cited references concerning the use of alkali metal borohydrides for treatment of ethoxylated products of any type or its possible use to provide perfume-grade chemicals.

SUMMARY OF THE INVENTION

It has now quite unexpectedly been discovered that the undesirable "metallic" odors typically associated with ethylene glycol monoaryl ethers produced by the base-catalyzed reaction of phenol with ethylene oxide can be substantially reduced, and in some instances completely eliminated, by treatment of the product with an alkali metal borohydride. By the process of this invention high quality ethylene glycol monoaryl ethers, particularly ethylene glycol monophenyl ether, having consistent odor profiles and suitable for use in fragrance applications are readily obtained. The present process is convenient and economical and makes it possible to convert ethylene glycol monoaryl ethers which were heretofore only useful as technical grade chemicals for industrial applications into highly useful perfume-grade products. Furthermore, the treatment process can be accomplished under ambient conditions with minimal equipment and without the development of color or loss of product.

The process of this invention involves contacting an ethylene glycol monoaryl ether, and particularly ethylene glycol monophenyl ether, with an alkali metal borohydride. The amount of alkali metal borohydride employed can range from 0.01 to 1 wt. percent, based on the ethylene glycol monoaryl ether, and more usually ranges from 0.05 to 0.5 wt. percent. Sodium borohydride is the preferred alkali metal borohydride. The ethylene glycol monoaryl ether and alkali metal borohydride are contacted at temperatures from ambient up to about 100° C. Preferably, the temperature is maintained below about 50° C. and the ethylene glycol monoaryl ether is sparged with steam after contacting with the alkali metal borohydride. For the sparging, up to about 10 weight percent water is subsurfacely introduced and dispersed into the ethylene glycol monoaryl ether which is maintained at an elevated temperature and reduced pressure. Most generally, 0.5 to 5 wt. percent water is employed while maintaining the ethylene glycol monoaryl ether at a temperature of 75° C.–120° C. and pressure less than 100 mm Hg.

DETAILED DESCRIPTION

The process of this invention involves the treatment of an ethylene glycol monoaryl ether with an alkali metal borohydride to substantially reduce, and in most cases completely eliminate, the objectionable metallic odor associated with such products which are produced by the monoethoxylation of phenol in an alkaline medium.

The process is adaptable for use with ethylene glycol monoaryl ethers of the general formula

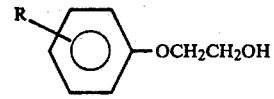

where R is hydrogen or an alkyl or alkoxyl group having from 1 to about 8 carbon atoms and which are obtained by the reaction of phenol and ethylene oxide in an alkaline medium. The process is particularly advantageous for use with ethylene glycol monophenyl ether.

The ethylene glycol monophenyl ether may be treated directly as it is obtained from the ethoxylation reactor or it may be neutralized with an organic or mineral acid and/or distilled prior to contacting with the alkali metal borohydride. In the situation where the product is neutralized, prior to treatment with the alkali metal borohydride it may be necessary to filter the product to remove insoluble salts. In an especially useful embodiment of this invention, substantially salt-free ethylene glycol monophenyl ether having a pH of 6 to 8 is treated with the alkali metal borohydride to obtain a highly useful perfume-grade product.

The alkali metal borohydride perferably employed is sodium borohydride, however, other alkali metal borohydrides such as lithium borohydride and potassium borohydride can also be utilized in the process. The amount of alkali metal borohydride employed for the treatment will vary depending on the history of the ethylene glycol monoaryl ether, i.e. the purity of reagents, type and amount of catalyst and reaction conditions employed in the ethoxylation reaction and whether the ethoxylated product has been neutralized, distilled or otherwise treated. In general, however, the amount of alkali metal borohydride used will range from about 0.01 to 1 weight percent, based on the ethylene glycol monoaryl ether. While larger quantities of the alkali metal borohydride can be employed, when the solubility limits of the ethylene glycol monoaryl ether are exceeded it is necessary to filter the product after treatment to remove the insoluble material. Most generally, the amount of alkali metal borohydride, preferably sodium borohydride, ranges from 0.05 up to 0.5 percent by weight.

The ethylene glycol monoaryl ether and alkali metal borohydride can be contacted at temperatures up to about 100° C. Most generally, however, the temperature will be maintained below 50° C. and in a preferred ebodiment of the invention treatment is accomplished at ambient temperature. Depending on the amount of alkali metal borohydride used, the ethylene glycol monoaryl ether may be utilized as such or the product may be filtered to remove insoluble salts present therein.

In a preferred embodiment of this invention, when reaction of the alkali metal borohydride is substantially completed, the ethylene glycol monoaryl ether is sparged with steam. Steam sparging is accomplished by subsurfacely introducing and dispersing up to 10 weight percent water into the product which is maintained at a temperature from 75° C. to 120° C. and at a pressure less than 100 mm Hg. The water is introduced through a sparge ring or other suitable apparatus. Preferably, from 0.5 to 5 weight percent water is introduced and the sparging operation is carried out at a temperature of 90° C. to 110° C. and pressure less than 50 mm Hg. The product is then dried to a moisture level less than 1 percent, and more preferably, less than 0.5 percent. This is typically accomplished by discontinuing the addition of water while maintaining the vacuum and heating.

The invention is more fully illustrated by the following examples:

EXAMPLE I

Ethylene glycol monophenyl ether was prepared by reacting phenol and ethylene oxide in an alkaline medium. The product contained 556 ppm phenol, had a distinct metallic odor, and had a color of 75/93 (percent transmittance measured at 440 and 550 m$\mu$). One kilogram of the product was charged to a glass vessel and 1 gram (0.1 wt. %) sodium borohydride powder added. There was a noticeable evolution of gas upon addition of the sodium borohydride. The mixture was agitated for 2 hours at room temperature after which time essentially all of the sodium borohydride was dissolved. The mixture was then allowed to stir for 14 additional hours under ambient conditions. At the end of this period, the ethylene glycol monophenyl ether had no detectable metallic odor and the color of the product was also improved to 97/98. The resulting ethylene glycol monophenyl ether had a pleasant mild rose odor with subtle fresh green nuances and was useful in fragrance applications as such, without any further treatment or purification. The product is highly useful and desirable extender for the rose note of phenethyl alcohol in various fragrance formulations. For example, formulating 5 parts phenethyl alcohol, 2 parts d-citronellol, 2 parts l-citronellol, 5 parts geraniol and 1.5 parts of the ethylene glycol monophenyl ether yields a fragrance having excellent rose notes.

EXAMPLE II

Example I was repeated except that 0.2 wt. percent sodium borohydride was employed. The ethylene glycol monophenyl ether obtained after treatment had a mild rose odor with no evidence of undesirable metallic notes and had a color of 97/98. A portion of the treated product is neutralized to pH of approximately 7 and employed without difficulty in various fragrance formulations.

EXAMPLE III

In a manner similar to that described in Example I, 200 mls ethylene glycol monophenyl ether was heated under a nitrogen atmosphere and 0.5 weight percent sodium borohydride added. The mixture was stirred for one hour and then filtered after the addition of approximately 2 grams of a filter aid (diatomaceous earth). There was no trace of the undesirable metallic odor originally present in the ethylene glycol monophenyl ether in the resulting treated product which had a color of 94/99.

EXAMPLE IV

To demonstrate the ability to further refine and enhance the fragrance qualities of the ethylene glycol monophenyl ether, Example I was repeated, however, at the conclusion of the sodium borohydride treatment the product was sparged with water/steam. For this process, after treatment with the sodium borohydride the ethylene glycol monophenyl ether was divided into three equal portions which were sparged with 5, 2 and 1 weight percent water/steam, respectively. The sparging was accomplished by subsurfacely introducing the water through a sparge tube into the ethylene glycol monophenyl ether maintained at a temperature of approximately 80° C. at a rate such that a pressure of 5 mm Hg was maintained. Vigorous agitation was maintained throughout the sparging operation to further disperse the water/steam within the ethylene glycol monophenyl ether. When all of the water was added, vacuum and heating were continued for an additional period until the moisture level of the product was reduced to about 0.1 percent. The products obtained by each of these treatments had excellent color with no detectable metallic odor. Ethylene glycol monophenyl ether products having a pleasant mild rose fragrance and having a more consistent odor profile are obtained in this manner.

EXAMPLE V

Commercial ethylene glycol monophenyl ether (Dowanol ® EPH; 98+% phenoxyethanol; 2000 ppm phenol, color 99/100) having a pronounced metallic odor was treated in accordance with the process of this invention. For the treatment, the product was heated with a 0.5 wt. percent sodium borohydride at 60° C. with agitation under a nitrogen atmosphere. After one hour the ethylene glycol monophenyl ether was filtered through a diatomaceous earth bed and then sparged with 1.5 weight percent water at 100°–110° C. and 4–6 mm Hg in accordance with the procedure described in Example IV. At the completion of the sparging, the product was dried for 30 minutes. There was no detectable metallic odor associated with the resulting ethylene glycol monophenyl ether product. Similar results are obtained when the above process is repeated using 4-isopropylphenoxyethanol.

I claim:

1. A process for enhancing the fragrance qualities of ethylene glycol monoaryl ethers obtained by the reaction of phenol with ethylene oxide in an alkaline reaction medium and having the formula

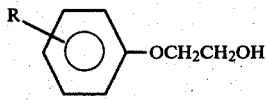

wherein R is hydrogen, a $C_{1-8}$ alkyl group or $C_{1-8}$ alkoxyl group which comprises intimately contacting the ethylene glycol monoaryl ether with 0.01 to 1 weight percent alkali metal borohydride at a temperature up to about 100° C., sparging by subsurfacely introducing and dispersing up to 10 weight percent water into the ethylene glycol monoaryl ether at a temperature of 75° C. to 120° C. and pressure less than 100 mm Hg, and drying the ethylene glycol monoaryl ether to a moisture content less than 1 percent.

2. The process of claim 1 wherein the ethylene glycol monoaryl ether is essentially free of insoluble salts and has a pH of 6 to 8.

3. The process of claim 1 wherein the alkali metal borohydride is selected from the group consisting of lithium borohydride, sodium borohydride and potassium borohydride.

4. The process of claim 3 wherein the ethylene glycol monoaryl ether is ethylene glycol monophenyl ether and the alkali metal borohydride is sodium borohydride.

5. The process of claim 4 wherein the sodium borohydride is present in an amount from 0.05 to 0.5 weight percent and the sparging is carried out at a temperature from 90° C. to 110° C. and pressure less than 50 mm Hg.

6. The process of claim 5 wherein 0.5 to 5 weight percent water is employed for sparging and the product is dried to a moisture content of less than 0.5 percent.

* * * * *